(12) United States Patent
Bradway et al.

(10) Patent No.: US 10,925,713 B2
(45) Date of Patent: Feb. 23, 2021

(54) STITCH WIRE ROUTING AND DELIVERY SYSTEM

(71) Applicant: Cook Medical Technologies LLC, Bloomington, IN (US)

(72) Inventors: Ryan C. Bradway, West Lafayette, IN (US); Kevin D. Wilger, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 156 days.

(21) Appl. No.: 16/056,764

(22) Filed: Aug. 7, 2018

(65) Prior Publication Data

US 2020/0046486 A1 Feb. 13, 2020

(51) Int. Cl.
*A61F 2/07* (2013.01)

(52) U.S. Cl.
CPC .......... *A61F 2/07* (2013.01); *A61F 2002/075* (2013.01); *A61F 2240/001* (2013.01)

(58) Field of Classification Search
CPC ........ A61F 2/07; A61F 2/95; A61F 2002/075; A61F 2002/9505; A61F 2002/9511
See application file for complete search history.

(56) References Cited

U.S. PATENT DOCUMENTS

| | | |
|---|---|---|
| 6,884,260 B2 | 4/2005 | Kugler et al. |
| 7,399,314 B2 | 7/2008 | Butaric et al. |
| 7,981,148 B2 | 7/2011 | Aguilar et al. |
| 8,226,703 B2 | 7/2012 | Caldarise et al. |
| 8,771,333 B2 | 7/2014 | Rincon |
| 9,427,307 B2 | 8/2016 | Pearson et al. |
| 9,700,400 B2 | 7/2017 | Havel |
| 9,839,542 B2 | 12/2017 | Bruszewski et al. |
| 9,855,155 B2 | 1/2018 | Majercak |
| 2004/0111146 A1 | 6/2004 | McCullagh et al. |
| 2011/0071614 A1 | 3/2011 | Majercak et al. |
| 2017/0189212 A1* | 7/2017 | Eller ........................ A61F 2/954 |

* cited by examiner

*Primary Examiner* — Melanie R Tyson
(74) *Attorney, Agent, or Firm* — Brinks Gilson & Lione

(57) ABSTRACT

The disclosure is directed to a continuous stitch wire routing and delivery system. The system includes a transitional stitching on a tube of a stent graft. The transitional stitching includes a distal portion stitching and a proximal portion stitching. A portion of each stitch loop of the stitches of the transitional stitching is disposed outside the tube and having a string passing through the stitch loop. A distal portion of the string passes through stitch loops of the distal portion stitching, a middle portion of the string is circumferentially around the tube, and a proximal portion of the string passes through stitch loops of the proximal portion stitching. The stent graft is in a compressed state when a tension of the string is above a high-tension threshold. The stent graft is in an expanded state when the tension is below a low-tension threshold.

19 Claims, 14 Drawing Sheets

```
┌─────────────────────────────────────────────────────────────────┐
│   disposing a circumferential stitching on the tube of the stent graft, │
│ wherein the circumferential stitching comprises a plurality of stitches │
│       arranged along a circumferential direction of the tube  1210      │
└─────────────────────────────────────────────────────────────────┘
                                  │
                                  ▼
┌─────────────────────────────────────────────────────────────────┐
│  disposing a portion of each stitch loop of the circumferential stitching │
│                          outside the tube                               │
│                                                            1220         │
└─────────────────────────────────────────────────────────────────┘
```

FIG. 12A

```
┌─────────────────────────────────────────────────────────────────┐
│   passing the middle portion of the string through stitch loops of the  │
│                       circumferential stitching                         │
│                                                            1230         │
└─────────────────────────────────────────────────────────────────┘
```

FIG. 12B interlacing a stitch of the proximal portion stitching with the joining stitch of the distal portion stitching
1240

FIG. 12C passing the proximal portion of the string through a stitch loop of the joining stitch of the distal portion stitching
1250

FIG. 12D passing the proximal portion of the string through a stitch loop of the first joining stitch of the distal portion stitching
1260 passing the distal portion of the string through a stitch loop of the second joining stitch of the proximal portion stitching
1270

FIG. 12E

STITCH WIRE ROUTING AND DELIVERY SYSTEM

BACKGROUND

1. Technical Field

The present disclosure relates to a system to control a stent graft. In particular, the present disclosure relates to a system to control the delivery of the stent graft.

2. Background Information

Some stent grafts, such as those located in the aorta, require to be placed precisely. From this point, the clinicians want to have a system so that they can control a stent graft by controlling the compression and expansion of the stent graft. During the delivery process of the stent graft, many factors may affect the final landing location of the stent graft. For example, one factor is the jump that occurs between the intermediate and final diameters. The blood flow and other factors may also impact the trajectory of the stent graft during its final landing process.

The present disclosure is directed toward addressing one or more drawbacks, including but not limited to those set forth above.

BRIEF SUMMARY

The present disclosure is directed to a system for controlling a stent graft. The system includes a transitional stitching disposed on a tube of a stent graft, the transitional stitching comprising more than one stitches, each stitch of the transitional stitching comprising a stitch loop, wherein the transitional stitching comprises a distal portion stitching, and a proximal portion stitching. The system includes a portion of each stitch loop disposed outside the tube and having a string passing through the stitch loop outside the tube. The string includes a distal portion, a middle portion, and a proximal portion. The distal portion of the string passes through stitch loops of the distal portion stitching. The middle portion of the string is disposed circumferentially around the tube. The proximal portion of the string passes through stitch loops of the proximal portion stitching. Furthermore, the stent graft is compressed when tension placing upon the string is larger than a tension threshold.

The present disclosure also describes a method for controlling a stent graft. The method includes disposing a transitional stitching on a tube of a stent graft. The transitional stitching includes more than one stitches, each stitch of the transitional stitching includes a stitch loop. The transitional stitching comprises a distal portion stitching, and a proximal portion stitching. The method also includes disposing a portion of each stitch loop outside the tube and passing a string through the stitch loop outside the tube. The string includes a distal portion, a middle portion, and a proximal portion. The method includes passing the distal portion of the string through stitch loops of the distal portion stitching, disposing the middle portion of the string circumferentially around the tube, and passing the proximal portion of the string through stitch loops of the proximal portion stitching. The method further includes placing, upon the string, tension larger than a tension threshold so that the stent graft is compressed.

The present disclosure also describes an apparatus for controlling a stent graft. The apparatus includes a stent graft. The stent graft includes a tube. The apparatus includes a transitional stitching disposed on the tube of the stent graft. The transitional stitching includes more than one stitches and each stitch includes a stitch loop. The apparatus also includes a string passing through stich loops of the transitional stitching. The stent graft is compressed when tension placing upon the string is larger than a tension threshold.

BRIEF DESCRIPTION OF THE DRAWINGS

FIGS. 12A, 12B, 12C, 12D, and 12E are flow diagrams of steps in a method for controlling a stent graft.

DETAILED DESCRIPTION OF THE DRAWINGS

Figure 1A:
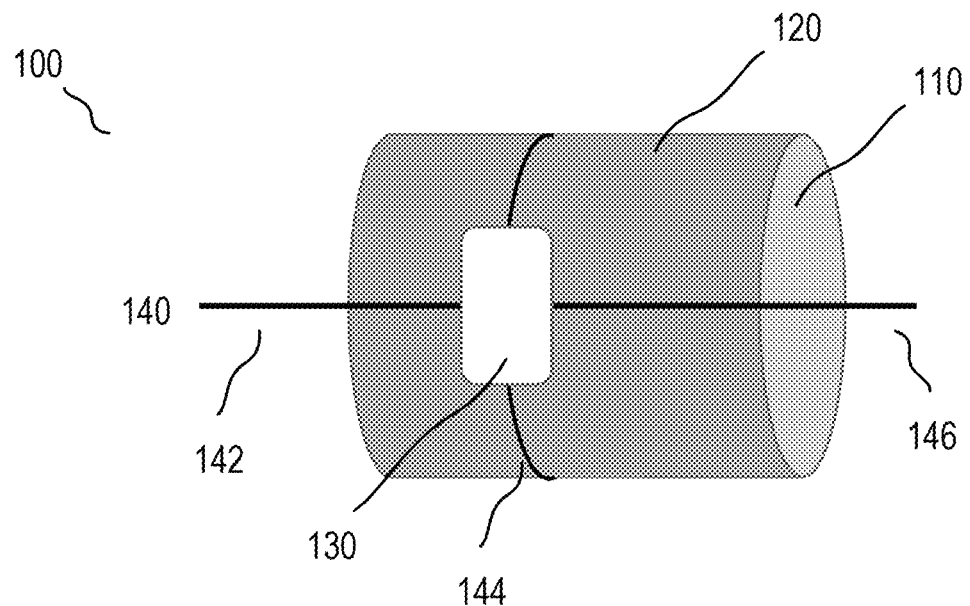
FIG. 1A is a schematic diagram of a stent graft with stitch wire routing when the stent graft in an expanded state.

The invention will now be described in detail hereinafter with reference to the accompanied drawings, which form a part of the present invention, and which show, by way of illustration, specific examples of embodiments. Please note that the invention may, however, be embodied in a variety of different forms and, therefore, the covered or claimed subject matter is intended to be construed as not being limited to any of the embodiments to be set forth below. Please also note that the invention may be embodied as methods, devices, components, or systems. Accordingly, embodiments of the invention may, for example, take the form of hardware, software, firmware or any combination thereof.

Throughout the specification and claims, terms may have nuanced meanings suggested or implied in context beyond an explicitly stated meaning. Likewise, the phrase "in one embodiment" or "in some embodiments" as used herein does not necessarily refer to the same embodiment and the phrase "in another embodiment" or "in other embodiments" as used herein does not necessarily refer to a different embodiment. It is intended, for example, that claimed subject matter includes combinations of exemplary embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

When a stent graft is delivered to a treatment location in a patient, it is desirable that an expansion state of the stent graft can be controlled during delivery. Thus, the precise placement of the stent graft can be controlled and achieved. The present disclosure describes a system and a method of controlling the expansion state of the stent graft. The present disclosure addresses the previously existing drawbacks, which occur when a final placement of the stent graft is different from an intended placement of the stent graft.

The present disclosure would be used by a health care provider to allow for the controlled release and compression of the stent graft. A string made would protrude from the delivery system proximally up the stent graft, circumferentially around a fabric tube of the stent graft, and again distally around the delivery system tip. By controlling the tension in the string, a diameter of the fabric tube of the stent graft can be selectively adjusted.

In one embodiment, the string may encompass a low friction and abrasive resistant string or wire. The string may comprise one or multiple filaments and may be made from a metal or yarn, for example and not limited to, a synthetic or natural fiber or flexible metal.

Figure 1B:
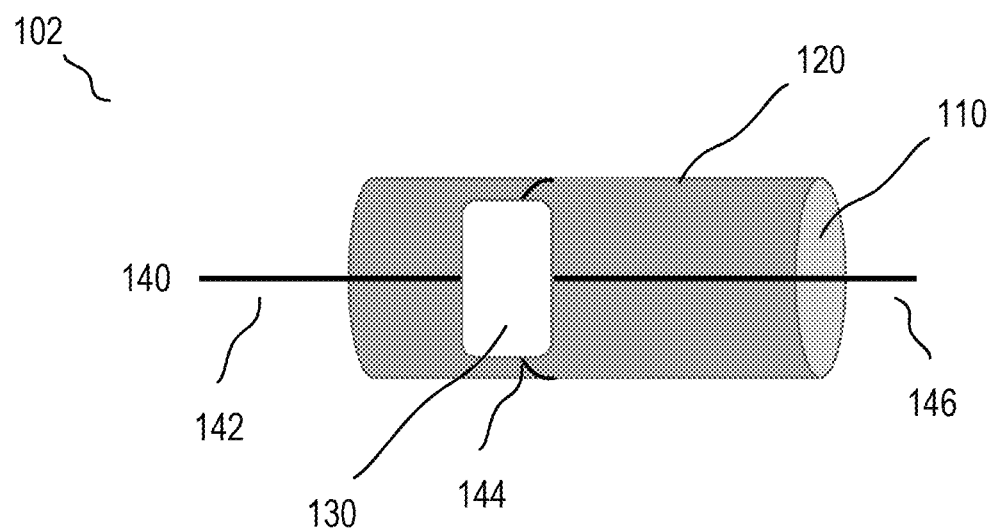
FIG. 1B is a schematic diagram of a stent graft with stitch wire routing when the stent graft in a compressed state.

FIGS. 1A and 1B show a schematic diagram of a tube 120 of a stent graft 110 in an expanded state 100 and in a compressed state 102, respectively. The tube 120 may be made from compliant materials, for example but not limited to, a fabric material. When the fabric tube 120 of the stent graft 110 is in the expanded state 100, the overall outer diameter of the fabric tube 120 may be a first diameter. For example and not limited to, the first diameter may be between 36 millimeter (mm) and 26 mm. When the fabric tube 120 of the stent graft 110 is in the compressed state 102, the overall diameter of the fabric tube 120 may be a second diameter, and the second diameter may be smaller than the first diameter. For example and not limited to, the second diameter may be between 15 mm and 10 mm.

The fabric tube of the stent graft may also be in a state between the expanded state 100 and the compressed state 102, so that the diameter of the fabric tube of the stent graft may be a number between the first diameter and the second diameter.

As shown in FIGS. 1A and 1B, a transitional stitching 130 is disposed on the fabric tube 120 of the stent graft 110. The transitional stitching may include one or more stitches. Each stitch of the transitional stitching may include a stitch loop. The one or more stitches are weaved through the fabric of the fabric tube, so that a portion of the stitch loop is outside the fabric tube and a portion of the stitch loop is inside the fabric tube.

The one or more stitches may be any stitch type to form stitch loops so that a string can feed through the stitch loops. The type of the stitching may be, for example and not limited to, blanket stitching, straight stitching, running stitching, cross stitching, and chain stitching. The one or more stitches may have a certain spacing between adjacent stitches, for example, the one or more stitches may be 1 millimeter apart from each other. In other embodiment, the one or more stitches may have almost no spacing between adjacent stitches, for example, the adjacent stitches are weaved closely next to each other.

Figure 2:
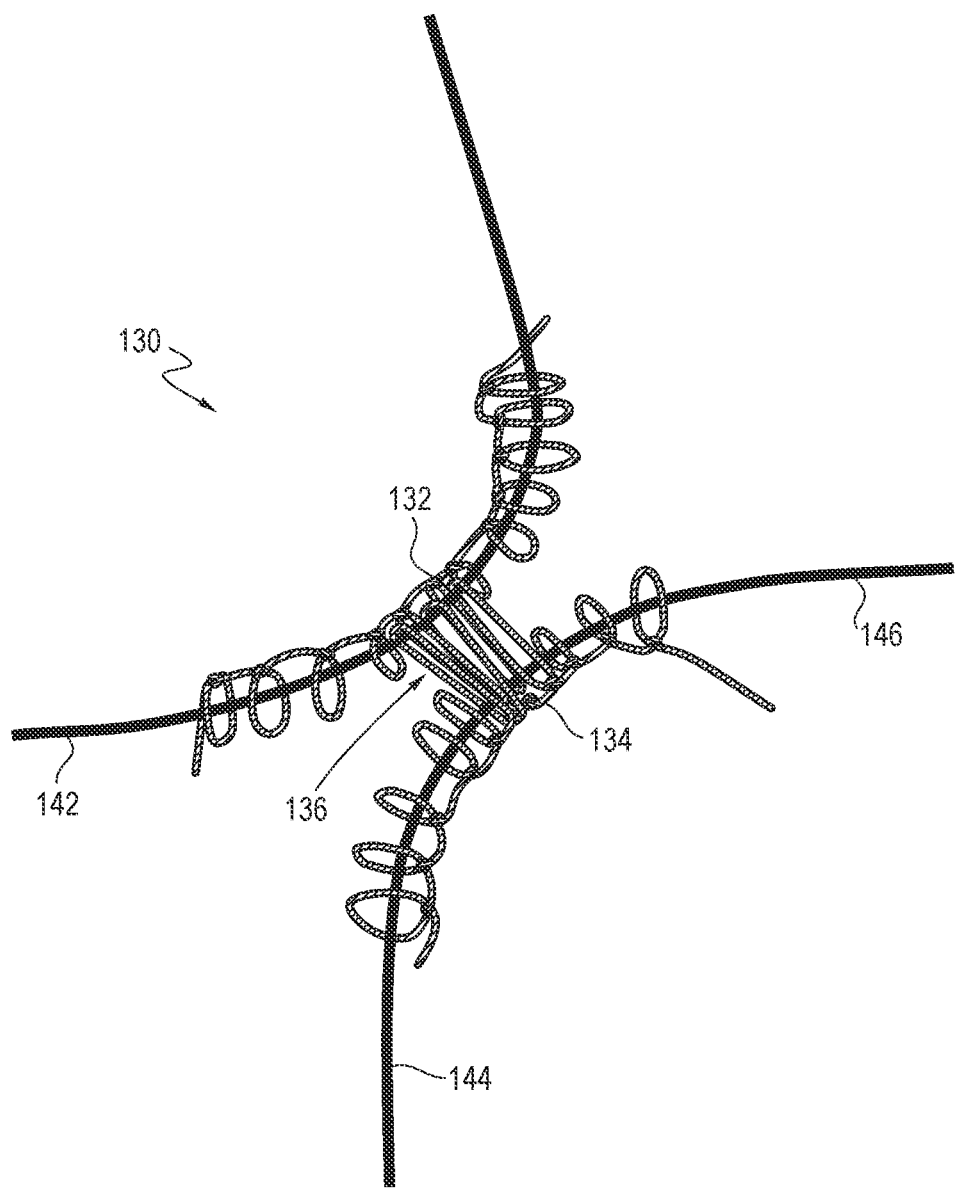
FIG. 2 is a schematic diagram of an embodiment of a transitional stitching.

In one embodiment as shown in FIG. 2, the transitional stitching 130 may include a distal portion stitching 132 and a proximal portion stitching 134.

The distal portion stitching 132 may include one or more stitches. The one or more stitches may be a first stitching type. The first stitching type may be, for example and not limited to, blanket stitching, straight stitching, running stitching, cross stitching, and chain stitching. In one embodiment, the distal portion stitching 132 may include between 8 and 12 stitches inclusively. In another embodiment, the one or more stitches of the distal portion stitching 132 may include several different stitch types.

The proximal portion stitching 134 may include one or more stitches. The one or more stitches of the proximal portion stitching 134 may be a second stitching type. The second stitching type may be, for example and not limited to, blanket stitching, straight stitching, running stitching, cross stitching, and chain stitching. The second stitching type may be the same as the first stitching type. In other embodiment, the second stitching type may be different as the first stitching type. In one embodiment, the proximal portion stitching 134 may include between 8 and 12 stitches inclusively. In another embodiment, the one or more stitches of the proximal portion stitching 134 may include several different stitch types.

The distal portion stitching 132 may further include one or more joining stitches 136. The joining stitches 136 join the distal portion stitching 132 with the proximal portion stitching 134. In one embodiment, the distal portion stitching 132 may include between 1 and 3 joining stitches inclusively.

As shown in FIGS. 1A and 1B, a string 140 may be disposed on the fabric tube 120 of the stent graft 110. The outer diameter of the string may be between 0.3 millimeter and 1 millimeter.

The string 140 may include a distal portion 142, a middle portion 144, and a proximal portion 146. The distal portion 142 extends towards a distal portion of the fabric tube 120 of the stent graft 110. The middle portion 144 is disposed circumferentially around the fabric tube 120 of the stent graft 110. The proximal portion 146 extends towards a proximal portion of the fabric tube 120 of the stent graft 110.

As shown in FIG. 2, the distal portion 142 of the string is configured to pass through the distal portion stitching 132 of the transitional stitching 130. The middle portion 144 of the string is disposed circumferentially around the fabric tube. A distal end of the middle portion 144 may feed through the distal portion stitching 132, and a proximal end of the middle portion 144 may feed through the proximal portion stitching 134.

The one or more stitches in the transitional stitching 130 form stitch loops. One portion of each of the stitch loops is disposed outside the fabric tube, and one portion of each of the stitch loops is disposed inside the fabric tube. The string 140 may feed through the stitch loops outside the fabric tube. Therefore, an inner diameter of the stitch loops may be slightly larger than an outer diameter of the string. For example, in one embodiment, the outer diameter of the string may be slightly smaller than 0.45 millimeter and the inner diameter of the stitch loops may be larger than or equal to 0.45 millimeter.

A user may control a tension of the string 140 to vary a state of the fabric tube 120 of the stent graft 110. When the tension of the string 140 is low, for example, lower than a low-tension threshold, the stent graft may be in an expanded state and may have a first diameter. When the tension of the string 140 is high, for example, above a high-tension threshold, the stent graft may be in a compressed state and may have a second diameter. The first diameter is larger than the second diameter. When the tension of the string 140 is between the low-tension threshold and high-tension threshold, the stent graft may be in the state between the compressed state and the expanded state, and the diameter of the stent graft may be a number between the first diameter and the second diameter.

Figure 3:
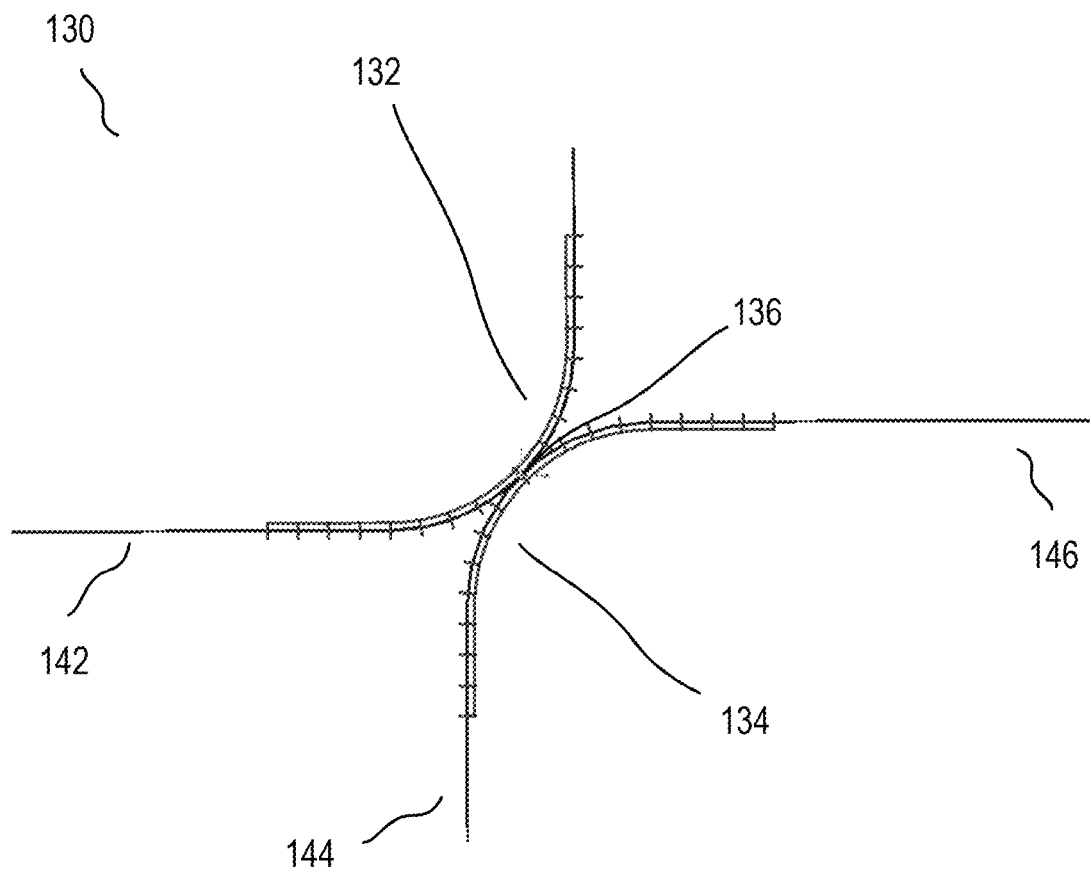
FIG. 3 is a schematic diagram of an embodiment of a transitional stitching.

In another embodiment as shown in FIG. 3, a transitional stitching 130 may include a distal portion stitching 132 and a proximal portion stitching 134, where the distal portion stitching 132 and the proximal portion stitching 134 may have similar shapes. The distal portion stitching 132 may include one or more stitches. The proximal portion stitching 134 may include one or more stitches. The distal portion stitching 132 may further include one or more joining stitches 136. A distal portion 142 of the string is configured to pass through the distal portion stitching 132 of the transitional stitching 130. The middle portion 144 of the string is disposed circumferentially around the fabric tube. A distal end of the middle portion 144 may feed through the distal portion stitching 132, and a proximal end of the middle portion 144 may feed through the proximal portion stitching 134.

Figure 4:
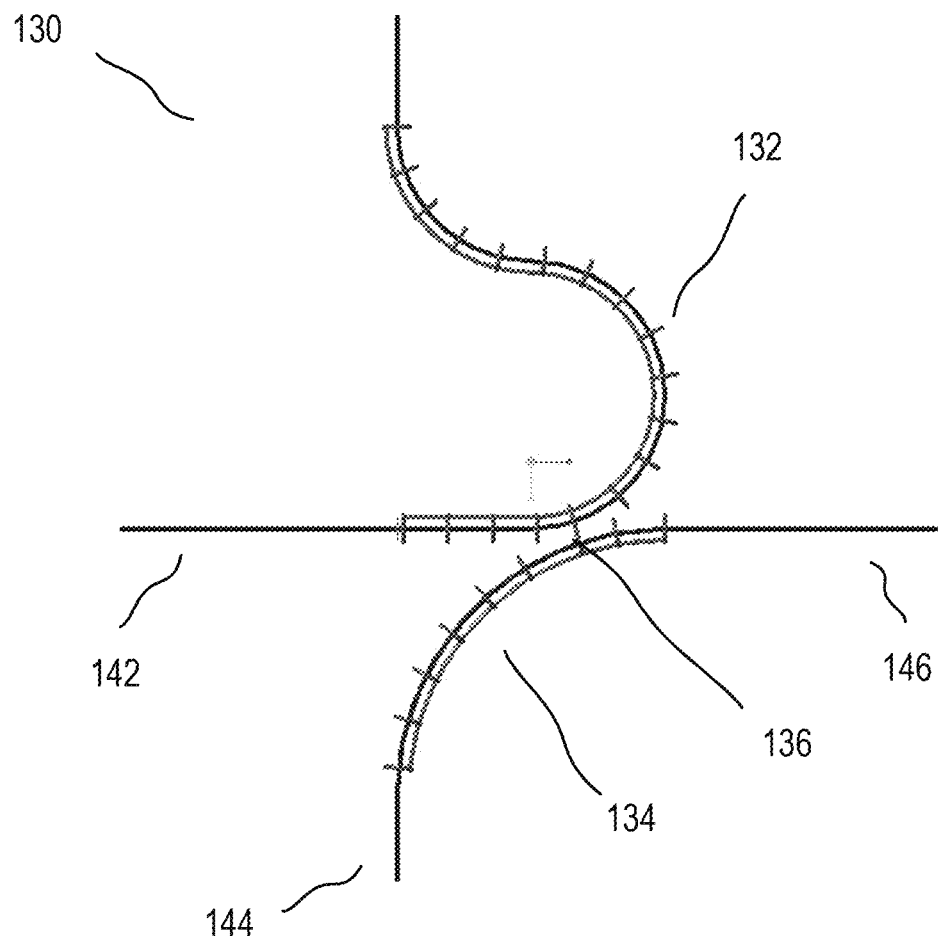
FIG. 4 is a schematic diagram of an embodiment of a transitional stitching.

In another embodiment as shown in FIG. 4, a transitional stitching 130 may include a distal portion stitching 132 and a proximal portion stitching 134, where the distal portion stitching 132 and the proximal portion stitching 134 may have different shapes. The distal portion stitching 132 may include one or more stitches. The proximal portion stitching 134 may include one or more stitches. The distal portion stitching 132 may further include one or more joining stitches 136. A distal portion 142 of the string is configured to pass through the distal portion stitching 132 of the transitional stitching 130. The middle portion 144 of the string is disposed circumferentially around the fabric tube. A distal end of the middle portion 144 may feed through the distal portion stitching 132, and a proximal end of the middle portion 144 may feed through the proximal portion stitching 134.

Figure 5:
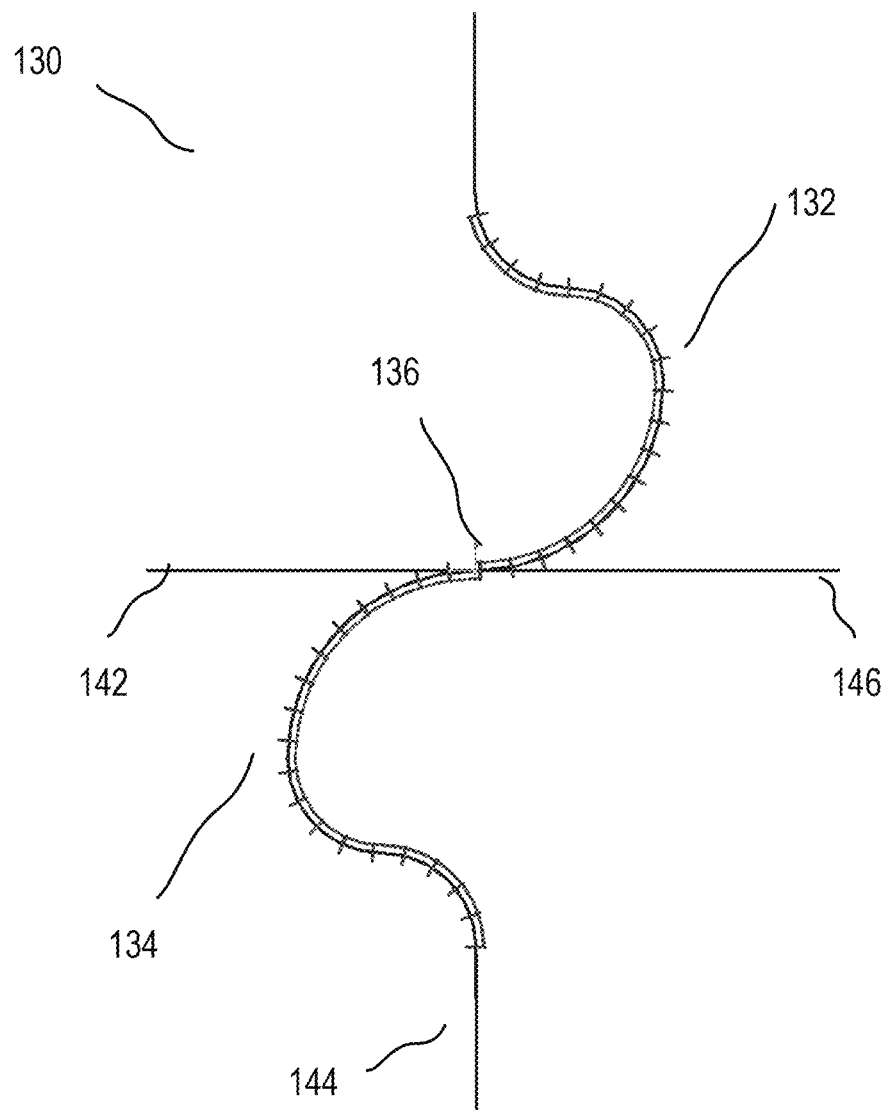
FIG. 5 is a schematic diagram of an embodiment of a transitional stitching.

In another embodiment as shown in FIG. 5, a transitional stitching 130 may include a distal portion stitching 132 and a proximal portion stitching 134, where the distal portion stitching 132 and the proximal portion stitching 134 may have similar shapes. The distal portion stitching 132 may include one or more stitches. The proximal portion stitching 134 may include one or more stitches. The distal portion stitching 132 may further include one or more joining stitches 136. A distal portion 142 of the string is configured to pass through the distal portion stitching 132 of the transitional stitching 130. The middle portion 144 of the string is disposed circumferentially around the fabric tube. A distal end of the middle portion 144 may feed through the distal portion stitching 132, and a proximal end of the middle portion 144 may feed through the proximal portion stitching 134.

Figure 6A:
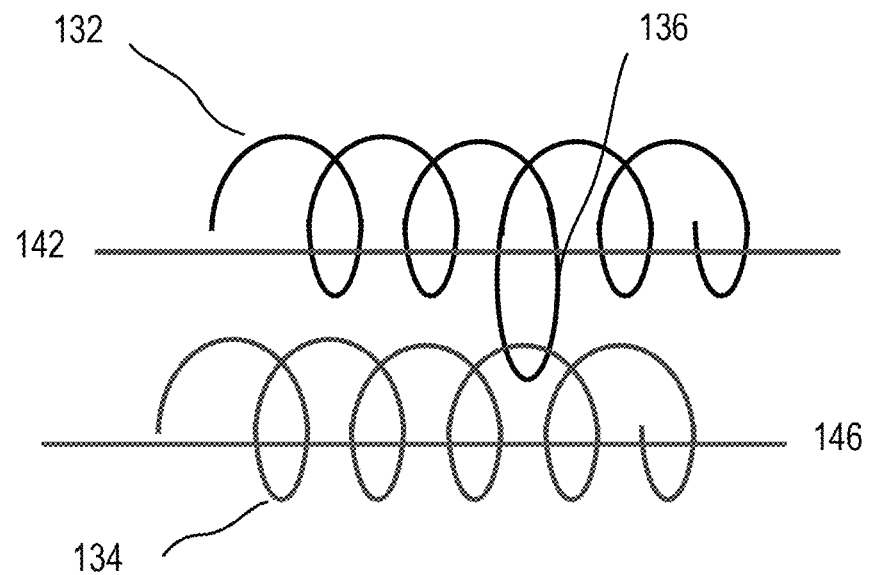
FIG. 6A is a schematic diagram of an embodiment of a joining stitch in a transitional stitching.
Figure 6B:
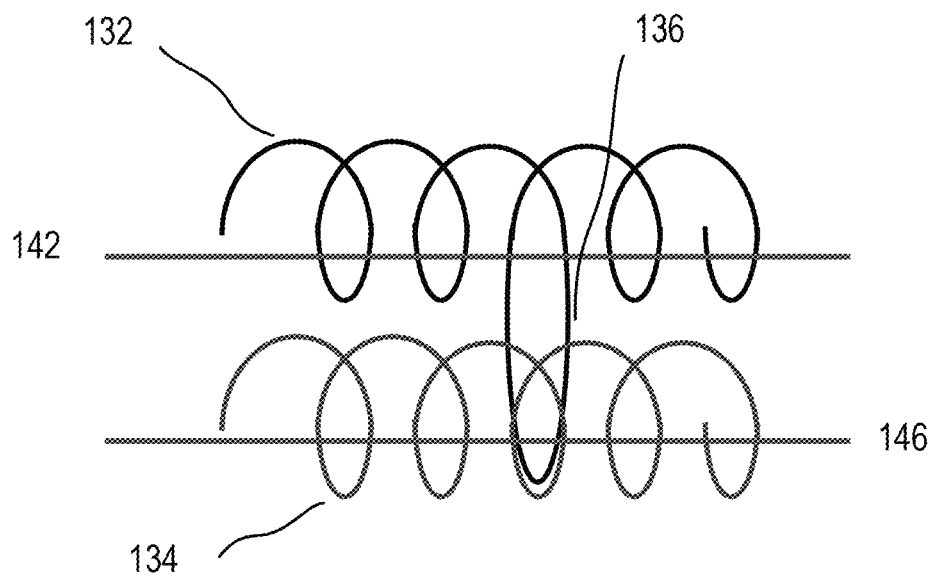
FIG. 6B is a schematic diagram of an embodiment of a joining stitch in a transitional stitching.
Figure 6C:
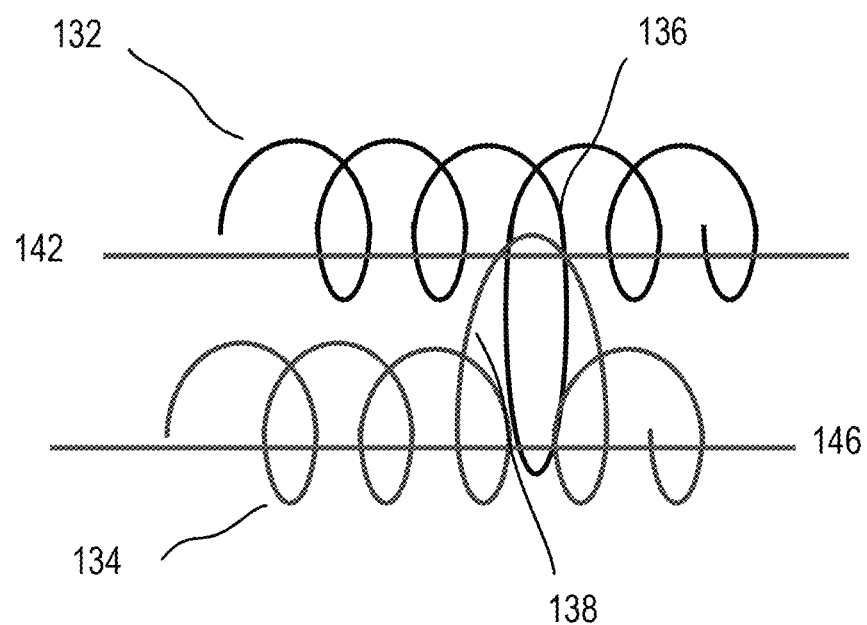
FIG. 6C is a schematic diagram of an embodiment of a joining stitch in a transitional stitching.

FIGS. 6A, 6B, and 6C describe several possible configurations for the joining stitches of the distal portion stitching in the transitional stitching.

As shown in FIG. 6A, one or more joining stitches 136 of a distal portion stitching 132 may interlace with one or more stitches of a proximal portion stitching 134. A distal portion 142 of a string is configured to pass through stitches of the distal portion stitching 132, and a proximal portion 146 of the string is configured to pass through stitches of the proximal portion stitching 134. In this embodiment, the proximal portion 146 of the string may not pass through the joining stitch 136 of the distal portion stitching 132.

As shown in FIG. 6B, one or more joining stitches 136 of a distal portion stitching 132 may have a larger stitch loop in comparison with other stitches. A distal portion 142 of a string is configured to pass through stitches of the distal portion stitching 132. A proximal portion 146 of the string is configured to pass through stitches of the proximal portion stitching 134 and pass through the one or more joining stitches 136. In this embodiment, the one or more joining stitches 136 may or may not interlace with one or more stitches of the proximal portion stitching 134.

As shown in FIG. 6C, one or more joining stitches 136 of a distal portion stitching 132 may have a larger stitch loop in comparison with other stitches of the distal stitching 132. One or more joining stitches 138 of a proximal portion stitching 134 may have a larger stitch loop in comparison with other stitches of the proximal stitching 134. A distal portion 142 of a string is configured to pass through stitches of the distal portion stitching 132 and pass through the one or more joining stitches 138. A proximal portion 146 of the string is configured to pass through stitches of the proximal portion stitching 134 and pass through the one or more joining stitches 136. In this embodiment, the one or more joining stitches 136 may or may not interlace with one or more stitches of the proximal portion stitching 134. In this embodiment, the one or more joining stitches 138 may or may not interlace with one or more stitches of the distal portion stitching 132.

Figure 7:
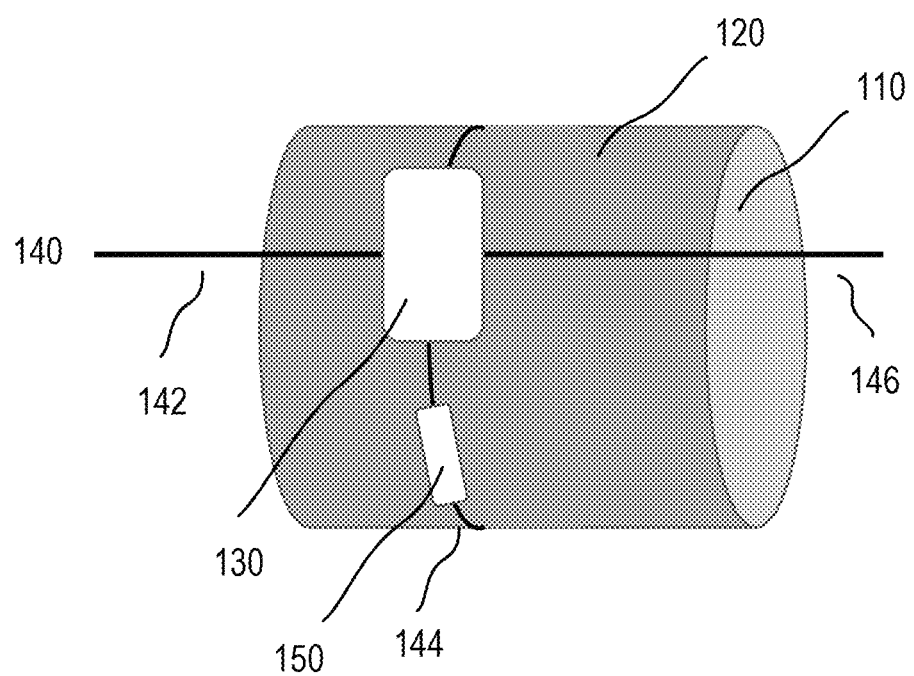
FIG. 7 is a schematic diagram of a stent graft with a transitional stitching and a circumferential stitching.

As shown in FIG. 7, there may be a circumferential stitching 150 disposed on the fabric tube 120 of the stent graft 110. The circumferential stitching may ensure that the constraining force of the string is applied at the centerline of the fabric tube of the graft stent, so that the fabric tube and the stent graft is reduced cylindrically and not conically. The circumferential stitching 150 may include one or more stitches. The one or more stitches may be arranged along a circumferential direction of the fabric tube.

The one or more stitches may be any stitch type to form stitch loops so that a string can feed through the stitch loops. An inner diameter of the stitch loops may be slightly larger than an outer diameter of the string. For example, in one embodiment, the outer diameter of the string may be slightly smaller than 0.45 millimeter and the inner diameter of the stitch loops may be larger than or equal to 0.45 millimeter. A portion of each stitch loop of the circumferential stitching is disposed outside the fabric tube.

A stitch type of the circumferential stitching 150 may be, for example and not limited to, blanket stitching, straight stitching, running stitching, cross stitching, and chain stitching. The stitches of the circumferential stitching 150 may have a certain spacing between adjacent stitches, for example, the adjacent stitches may be 1 millimeter apart from each other. In other embodiment, the adjacent stitches may almost have no spacing between them, for example, the adjacent stitches are disposed closely to each other. The circumferential stitching 150 may include any number of stitches, for example and not limited to, between three and six stitches inclusively.

Figure 8:
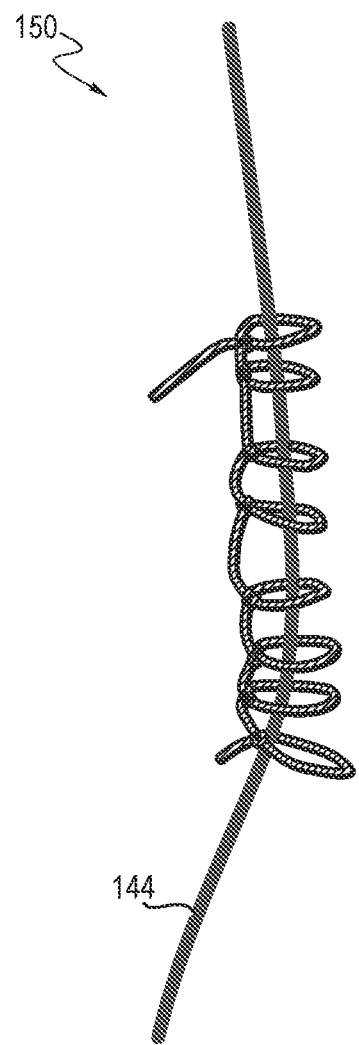
FIG. 8 is a schematic diagram of an embodiment of a circumferential stitching.

As shown in FIG. 8, a middle portion 144 of a string may pass through the circumferential stitching 150. The circumferential stitching 150 may provide support to stabilize the string when the string slides in the stitch loops of the circumferential stitching 150.

The circumferential stitching 150 may be disposed at any circumferential location relatively to the transitional stitching 130. In one embodiment, the circumferential stitching 150 may be disposed at a circumferential location 180 degree relatively to the transitional stitching 130.

In other embodiment, there may be more than one circumferential stitchings, for example and not limited to, two and three circumferential stitchings. The circumferential stitchings may be at certain circumferential locations relatively to the transitional stitching 130. For example, when there are two circumferential stitchings, the circumferential stitchings may be disposed at circumferential locations of 120 degree and 240 degree relatively to the transitional stitching 130; when there are three circumferential stitchings, three circumferential stitchings may be disposed at circumferential locations of 90 degree, 180 degree, and 270 degree relatively to the transitional stitching 130.

Figure 9:
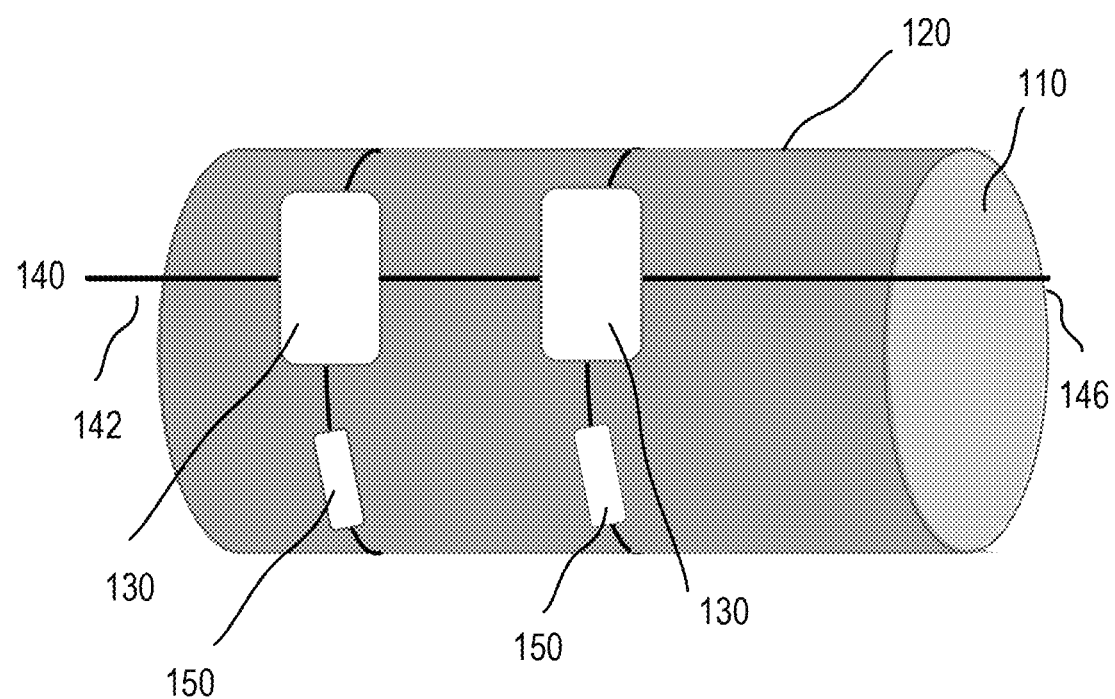
FIG. 9 is a schematic diagram of a stent graft with multiple transitional stitchings and multiple circumferential stitchings.

In another embodiment as shown in FIG. 9, there may be multiple transitional stitchings 130. For each transitional stitching, there may be one or more circumferential stitchings 150. The multiple transitional stitchings and circumferentially stitchings can ensure that the constraining force of the string is applied evenly on the fabric tube of the graft stent, so that the fabric tube and the stent graft is reduced from the expanded state to the compressed state cylindrically.

The present disclosure describes a system with a transitional stitching and a circumferential stitching. The transitional stitching allow for a smooth routing from axial to circumferential string to minimize their retraction force. The transitional stitching also provide an interface for force to be transmitted between the strings to reduce the diameter of the fabric tube of the grant stent. The circumferentially stitching can ensure that the constraining force of the string is applied at the centerline of the fabric tube of the graft stent, so that the fabric tube and the stent graft is reduced cylindrically and not conically. One advantage of the present disclosure is that proximal and distal fixation trigger wires are not needed to axially constrain the graft stent.

The present disclosure also describes a method. The method includes using a system for controlling a stent graft. The system may be any of the embodiments as described above.

Figure 10:
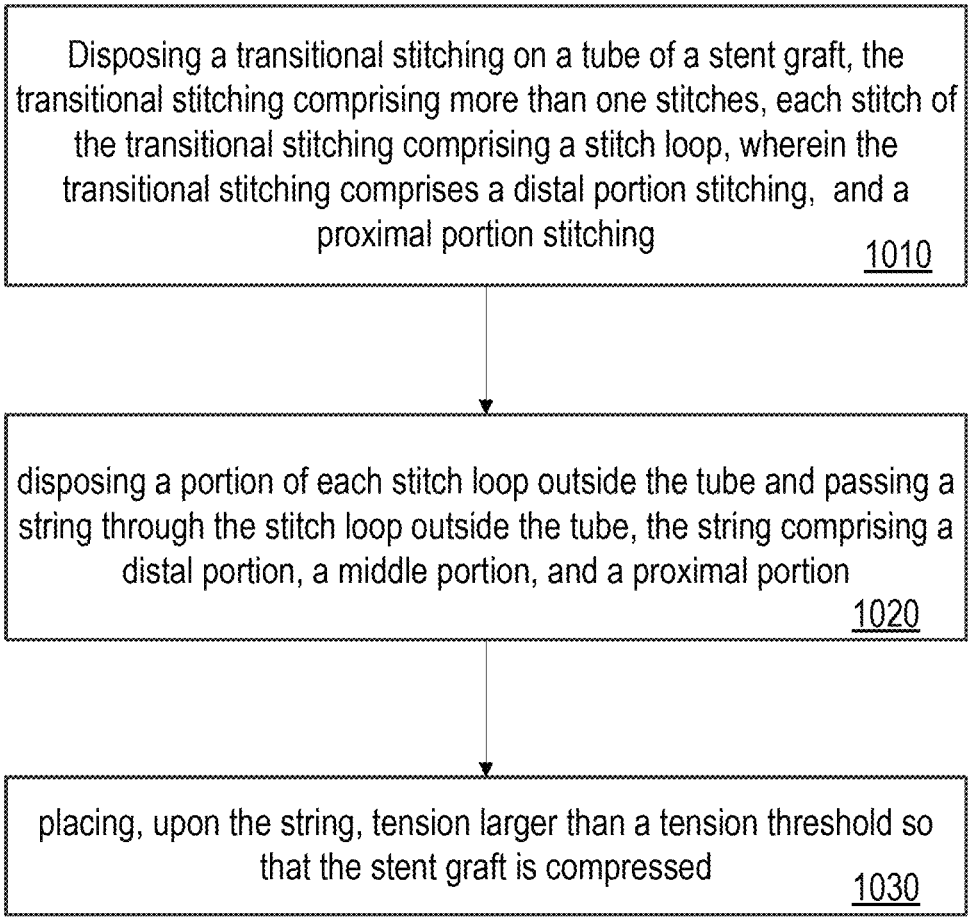
FIG. 10 is a flow diagram of a method for controlling a stent graft.

In one embodiment, a method for controlling a stent graft is shown in FIG. 10. The method includes step 1010: disposing a transitional stitching on a tube of a stent graft. The transitional stitching includes more than one stitches, each stitch of the transitional stitching includes a stitch loop. The transitional stitching comprises a distal portion stitching, and a proximal portion stitching.

The method also includes step 1020: disposing a portion of each stitch loop outside the tube and passing a string through the stitch loop outside the tube. The string includes a distal portion, a middle portion, and a proximal portion.

Figure 11:
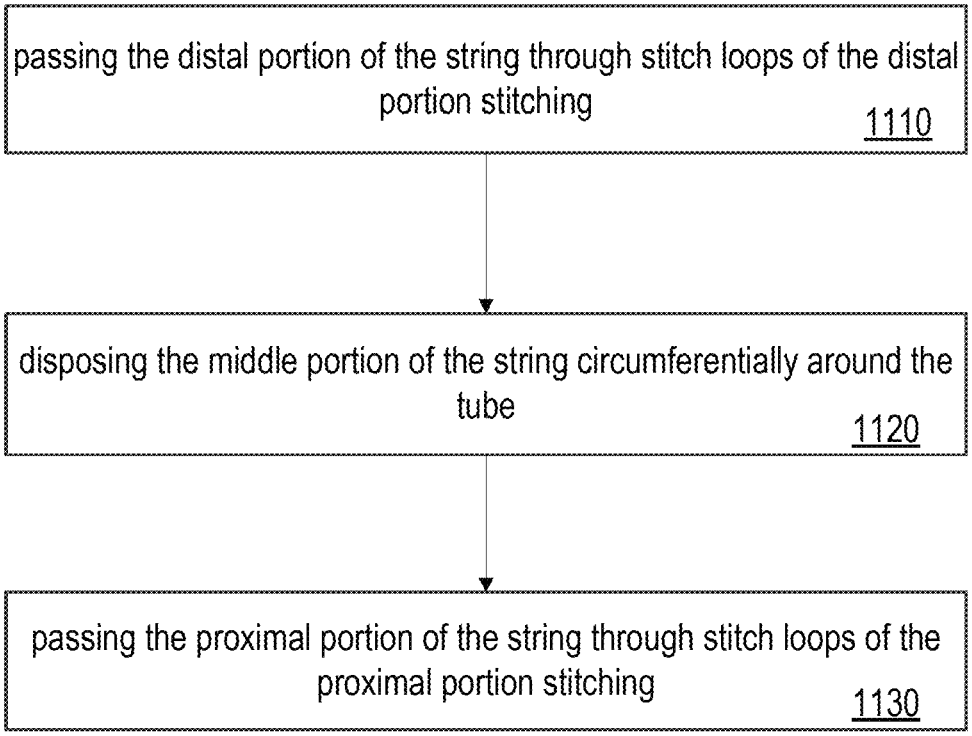
FIG. 11 is a flow diagram of a method for passing a string through stitch loops on a stent graft.

As shown in FIG. 11, step 1020 may include step 1110: passing the distal portion of the string through stitch loops of the distal portion stitching; step 1120: disposing the middle portion of the string circumferentially around the tube; and step 1130: passing the proximal portion of the string through stitch loops of the proximal portion stitching.

The method further includes step 1030: placing, upon the string, tension larger than a tension threshold so that the stent graft is compressed.

As shown in FIG. 12A, the method for controlling a stent graft in one embodiment may further include step 1210: disposing a circumferential stitching on the tube of the stent graft. The circumferential stitching comprises a plurality of stitches arranged along a circumferential direction of the tube. The method may further includes step 1220: disposing a portion of each stitch loop of the circumferential stitching outside the tube.

As shown in FIG. 12B, a method for controlling a stent graft in one embodiment may further include step 1230: passing the middle portion of the string through stitch loops of the circumferential stitching.

As shown in FIG. 12C, a method for controlling a stent graft in one embodiment may further have that the distal portion stitching comprises a joining stitch and include step 1240: interlacing a stitch of the proximal portion stitching with the joining stitch of the distal portion stitching.

As shown in FIG. 12D, a method for controlling a stent graft in one embodiment may further have that the distal portion stitching comprises a joining stitch and include step 1250: passing the proximal portion of the string through a stitch loop of the joining stitch of the distal portion stitching.

A method for controlling a stent graft in another embodiment may further have that the distal portion stitching comprises a first joining stitch and the proximal portion stitching comprises a second joining stitch. As shown in FIG. 12E, the method may further include step 1260: passing the proximal portion of the string through a stitch loop of the first joining stitch of the distal portion stitching and step 1270: passing the distal portion of the string through a stitch loop of the second joining stitch of the proximal portion stitching.

While the particular invention has been described with reference to illustrative embodiments, this description is not meant to be limiting. Various modifications of the illustrative embodiments and additional embodiments of the invention will be apparent to one of ordinary skill in the art from this description. Those skilled in the art will readily recognize that these and various other modifications can be made to the exemplary embodiments, illustrated and described herein, without departing from the spirit and scope of the present invention. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

The invention claimed is:

1. A system for controlling a stent graft, the system comprising:
    a transitional stitching disposed on a tube of a stent graft, the transitional stitching comprising more than one stitch, each stitch of the transitional stitching comprising a stitch loop, wherein the transitional stitching comprises a distal portion stitching, and a proximal portion stitching;
    a portion of each stitch loop disposed outside the tube and having a string passing through the stitch loop outside the tube, wherein:
        the string comprises a distal portion, a middle portion, and a proximal portion, the distal portion of the string passes through stitch loops of the distal portion stitching, the middle portion of the string is disposed circumferentially around the tube, and the proximal portion of the string passes through stitch loops of the proximal portion stitching; and wherein the stent graft is compressed when tension placed upon the string is larger than a tension threshold.

2. The system according to claim 1, further comprising:
a circumferential stitching disposed on the tube of the stent graft, wherein:
the circumferential stitching comprises a plurality of stitches arranged along a circumferential direction of the tube, each stitch of the circumferential stitching comprising a stitch loop, and
a portion of each stitch loop of the circumferential stitching is disposed outside the tube.

3. The system according to claim 2, wherein:
the middle portion of the string passes through the stitch loops of the circumferential stitching.

4. The system according to claim 2, wherein:
a number of stitches of the circumferential stitching is between 3 and 6 inclusive.

5. The system according to claim 2, wherein:
stitches of the circumferential stitching comprise a blanket stitch type.

6. The system according to claim 1, wherein:
the distal portion stitching comprises a joining stitch; and
a stitch of the proximal portion stitching interlaces with the joining stitch of the distal portion stitching.

7. The system according to claim 1, wherein:
the distal portion stitching comprises a joining stitch; and
the proximal portion of the string passes through a stitch loop of the joining stitch of the distal portion stitching.

8. The system according to claim 1, wherein:
the distal portion stitching comprises a first joining stitch; and
the proximal portion stitching comprises a second joining stitch.

9. The system according to claim 8, wherein:
the proximal portion of the string passes through a stitch loop of the first joining stitch of the distal portion stitching; and
the distal portion of the string passes through a stitch loop of the second joining stitch of the proximal portion stitching.

10. The system according to claim 1, wherein:
a number of stitches of the distal portion stitching is between 8 and 12 inclusive.

11. A method for controlling a stent graft, the method comprising:
disposing a transitional stitching on a tube of a stent graft, the transitional stitching comprising more than one stitch, each stitch of the transitional stitching comprising a stitch loop, wherein the transitional stitching comprises a distal portion stitching, and a proximal portion stitching;
disposing a portion of each stitch loop outside the tube and passing a string through the stitch loop outside the tube, the string comprising a distal portion, a middle portion, and a proximal portion, wherein the method comprises:
passing the distal portion of the string through stitch loops of the distal portion stitching,
disposing the middle portion of the string circumferentially around the tube, and
passing the proximal portion of the string through stitch loops of the proximal portion stitching; and
placing, upon the string, tension larger than a tension threshold so that the stent graft is compressed.

12. The method according to claim 11, further comprising:
disposing a circumferential stitching on the tube of the stent graft, wherein the circumferential stitching comprises a plurality of stitches arranged along a circumferential direction of the tube, each stitch of the circumferential stitching comprising a stitch loop; and
disposing a portion of each stitch loop of the circumferential stitching outside the tube.

13. The method according to claim 12, further comprising:
passing the middle portion of the string through the stitch loops of the circumferential stitching.

14. The method according to claim 11, wherein the distal portion stitching comprises a joining stitch, the method further comprising:
interlacing a stitch of the proximal portion stitching with the joining stitch of the distal portion stitching.

15. The method according to claim 11, wherein the distal portion stitching comprises a joining stitch, the method further comprising:
passing the proximal portion of the string through a stitch loop of the joining stitch of the distal portion stitching.

16. The method according to claim 11, wherein the distal portion stitching comprises a first joining stitch and the proximal portion stitching comprises a second joining stitch, the method further comprising:
passing the proximal portion of the string through a stitch loop of the first joining stitch of the distal portion stitching; and
passing the distal portion of the string through a stitch loop of the second joining stitch of the proximal portion stitching.

17. An apparatus for controlling a stent graft, the apparatus comprising:
a stent graft comprising a tube;
a transitional stitching disposed on the tube of the stent graft, the transitional stitching comprising more than one stitch and each stitch comprising a stitch loop, wherein the transitional stitching comprises a distal portion stitching, and a proximal portion stitching;
a string passing through stitch loops of the transitional stitching, wherein the stent graft is compressed when tension placed upon the string is larger than a tension threshold; and
wherein the string comprises a distal portion, a middle portion, and a proximal portion, wherein
the distal portion of the string passes through stitch loops of the distal portion stitching,
the middle portion of the string is disposed circumferentially around the tube, and
the proximal portion of the string passes through stitch loops of the proximal portion stitching.

18. The apparatus according to claim 17, further comprising:
a circumferential stitching disposed on the tube of the stent graft, wherein:
the circumferential stitching comprises a plurality of stitches arranged along a circumferential direction of the tube, each stitch of the circumferential stitching comprising a stitch loop, and
a portion of each stitch loop of the circumferential stitching is disposed outside the tube; and the string passes through the stitch loops of the circumferential stitching.

19. The apparatus according to claim 17, wherein:
the distal portion stitching comprises a joining stitch; and
a stitch of the proximal portion stitching interlaces with the joining stitch of the distal portion stitching.

\* \* \* \* \*